United States Patent [19]
Sato et al.

[11] Patent Number: 5,473,551
[45] Date of Patent: Dec. 5, 1995

[54] AUTOMATIC ANALYZER

[76] Inventors: Takeshi Sato, Tsukubadai-apartment 1-106, 663, Ichige; Katsuaki Takahashi, 2031-813, Tsuda, both of Katsuta-shi, Ibaraki-ken, Japan

[21] Appl. No.: 201,253

[22] Filed: Feb. 24, 1994

[30] Foreign Application Priority Data

Feb. 26, 1993 [JP] Japan .................................. 5-038134

[51] Int. Cl.$^6$ ................................................. G01N 35/00
[52] U.S. Cl. ........................... 364/496; 422/50; 364/499
[58] Field of Search .................................... 364/496, 499; 435/4; 204/153.1, 400; 422/50, 68.1

[56] References Cited

U.S. PATENT DOCUMENTS

| | | | |
|---|---|---|---|
| 4,459,265 | 7/1984 | Berglund | 422/64 |
| 4,536,369 | 8/1985 | Sakurada et al. | 422/65 |
| 4,636,360 | 1/1987 | Sakurada et al. | 422/65 |
| 4,695,430 | 9/1987 | Couille et al. | 422/65 |
| 4,935,106 | 6/1990 | Liston et al. | 204/153.1 |
| 5,125,748 | 6/1992 | Bjornson et al. | 356/414 |

FOREIGN PATENT DOCUMENTS

| | | | |
|---|---|---|---|
| 57-29996 | 6/1982 | Japan | C12Q 1/00 |
| 76464 | 4/1987 | Japan | G01N 33/78 |
| 286095 | 11/1990 | Japan | C12Q 1/00 |

*Primary Examiner*—Ellis B. Ramirez
*Assistant Examiner*—Patrick J. Assovad

[57] ABSTRACT

An automatic analyzer wherein a part exchange judging section judges whether or not the current time reached an exchange date of one of constituent parts of the automatic analyzer. When the part exchange judging section judges that the current time has reached the exchange date of one of the constituent parts, the part exchange judging section delivers a command to display an alarm notifying the exchange of the one of the constituent part on a CRT. A K-factor update judging section judges whether or not the part to be exchanged affects the K factor and the K factor is to be updated. When the K-factor update judging section judges that the K factor is to be updated, an alarm notifying the update of the K factor is displayed on the CRT. The alarm notifying the update of the K factor is displayed until the K factor is updated. Further, each of various kinds of standardized protocols is also automatically executed. When a start key is pushed on a keyboard, a standardized protocol selection screen appears on the CRT. When an operator enters a number indicative of one of the protocols on the keyboard in accordance with a message, a selected standardized protocol screen appears on the CRT. When the operator enters a reaction inducing substance for evaluation, an analysis reagent number, a concentration, a dilution sequence number and the number of measurements, measurement is started.

10 Claims, 10 Drawing Sheets

| TEMP : 37°C | STATUS : STAND-BY | ALARM ! | 93 / 12 / 20 | 12 : 00 |

WORKING INFORMATION

PHOTOMETRIC — 410a                    FILTER
1. CELLS    ?? 93 / 12 / 01 [ ]        6. SYRINGE   93 / 11 / 10 [ ]
2. LAMP    [!] 93 / 05 / 20 [①]        7. FRONT     93 / 11 / 10 [ ]
              411a        412a         8. REAR      93 / 11 / 10 [ ]

SEAL                                   K-FACTOR  PARTS No.        [2]
3. SERUM       93 / 10 / 01 [ ]        (1) NADH   93 / 05 / 20
4. REAGENT 1   93 / 10 / 01 [ ]   [!]  (2) 4-NP   93 / 05 / 20
5. REAGENT 2   93 / 10 / 01 [ ]   411d (3) 4-NA   93 / 05 / 20
                                       (4)
?? : CAUTION                           (5)
!! : OVER                              (6)

MEASURED RESULTS
REACTION INDUCING SUBSTANCE NAME : NADH

| SAMPLE | | BLANK | SEQUENCE 1 | SEQUENCE 2 | SEQUENCE 3 | SEQUENCE 4 | SEQUENCE 5 |
|---|---|---|---|---|---|---|---|
| ABSORBANCE (A) | 1 | −35 | 4025 | 8147 | 12100 | 16505 | |
| | 2 | −24 | 4070 | 8089 | 12089 | 16583 | |
| | 3 | −25 | 4055 | 8157 | 12203 | 16333 | |
| | 4 | −37 | 4040 | 8218 | 12175 | 16374 | |
| | 5 | −12 | 4074 | 8148 | 12113 | 16333 | |
| A bar | | −26.6 | 4052.8 | 8157.2 | 12136.0 | 16425.6 | |
| △A | | | 4026.2 | 8130.6 | 12109.4 | 16399.0 | |
| R．△A % | | | 100 | 100.9 | 100.3 | 101.8 | |
| K | | | 6814.7 | 6781.7 | 6848.9 | 6746.8 | |
| K bar | 6798 | | | | | | |
| SD | 43.8 | | | | | | |
| CV % | 0.64 | | | | | | |

AUTOMATIC ANALYZER

BACKGROUND OF THE INVENTION

The present invention relates to an automatic analyzer for clinical analysis and more particularly, is directed to an automatic analyzer which performs its own calibration in accordance with a standardized protocol used for correction of differences in measured data between the automatic analyzers of different facilities.

In clinical analysis fields, in recent years, it has been demanded to correct differences in measured data between automatic analyzers of different facilities, that is, standardize measured data. To this end, different standardized protocols are prescribed for different objects to be measured such as electrolyte, cholesterol and enzyme number.

Explanation will be made, in particular, in connection with the enzyme number. First, differences in measured data between the automatic analyzers result partly from the accuracies of the individual automatic analyzers. For the purpose of calibrating the automatic analyzers, standardized protocols have been prescribed (refer to "Standardized Protocol Manual", Japanese Association of Medical Technologists, compiled by Research Group of Clinical Chemistry, pp. 35–51, 1992).

According to the Standardized Protocol Manual, reaction product (which will be referred to as reaction inducing substance, hereinafter) for each enzyme such as Nicotinamide Adenine Dinucleotide Phosphate reduced-form (NADH) for Aspartate Aminotransferase and 4-Nitrophenol for amylase is directly or indirectly (actually, glucose is used for NADH) weighted, and the calibration is carried out manually by using the weighted reaction product as a standard solution.

JP-B-57-29996 discloses an enzyme analysis method for calculating an amount of enzyme in a test enzyme solution. In this enzyme analysis method, a device constant or K factor of each automatic analyzer is calculated and the amount of enzyme in the test sample solution is calculated on the basis of the device constant and the absorbance of the test enzyme solution.

SUMMARY OF THE INVENTION

The aforementioned K factor can be expressed by the following equation (1).

$$K=(1/\epsilon)\times(1/L)\times(V/v)\times10^6 \quad (1)$$

where $\epsilon$ is a molar absorbance, L is a light path length, v is a sample volume, and V is a total of the sample volume and a reagent volume.

Accordingly, after the K factor is set, if, for example, a light source (e.g., a lamp) for measuring the absorbance of a test sample is exchanged, the quantity of light passed through the test sample is changed, and hence a molar absorbance is varied and the K factor is also varied. If a cell or sample cuvette is exchanged, this causes the light path length L to vary, whereby the K factor is also varied. In an automatic analyzer, there are usually provided seals for preventing the solution of sample cuvettes or reagent cuvettes from leaking therefrom. If such seals are exchanged, the sample volume and reagent volume may be changed. Even in this case, the K factor might be varied.

In the prior art automatic analyzer, however, fluctuations in the K factor caused by part exchange, etc. has not been taken into consideration. Once the K factor is measured and set, the set K factor will not be modified even after the part exchange.

In this way, in the prior art, in spite of the fact that the K factor is varied by the part exchange, etc., the quantity of enzyme or the like in the test sample has been calculated on the basis of the K factor prior to the part exchange, with the result of a low measuring accuracy.

Further, in the prior art automatic analyzer, the complicated K-factor calculation based on the above standardized protocols has been carried out by using a different computer or the like without performing the calculation by itself automatically. For this reason, calculation of a device constant (K factor) must be manually carried out, which involves a lot of time and labor with low calculated accuracy of the K factor.

It is a first object of the present invention to realize an automatic analyzer which can automatically judge the necessity or non-necessity of updating a set K factor and when determining the necessity of updating the K factor, which can display an alarm notifying the update to thereby improve a test sample measurement accuracy.

A second object of the present invention is to realize an automatic analyzer which can automatically judge the necessity or non-necessity of updating a set K factor and when determining the necessity of updating the K factor, which can display an alarm notifying the update, and also which can automatically execute various kinds of standardized protocols to thereby improve a K-factor calculation accuracy and a test-sample characteristic measurement accuracy.

In accordance with an aspect of the present invention, the present invention is constituted so as to attain the above first object in a manner that, an automatic analyzer includes a test sample array unit on which test samples to be tested are arranged, a reagent array unit on which reagents are arranged, a measurement unit for adding the reagents into the test samples and measuring physical characteristics of the test samples, an input unit for entering a command set by an operator, and a display unit for displaying measured information thereon. The automatic analyzer comprises a memory section for storing a device constant of the automatic analyzer therein; a part exchange judging section for judging whether or not a major constituent part in the test sample array unit, reagent array unit and measurement section is to be exchanged; a device constant update judging section, when the part exchange judging section judges that the major constituent part is to be exchanged, for judging whether or not a device constant stored in the memory section is to be updated due to the exchange of the major constituent part to cause the display unit to display an alarm notifying update of the device constant; and an analyzing operation control section for controlling operations of the test sample array unit and the reagent array unit in accordance with the command entered by the input unit and for analyzing a specific item for the test sample on the basis of the physical characteristic measured by the measurement unit.

In the automatic analyzer, it is preferable that the part exchange judging section stores an exchange date of the major constituent part in the test sample array unit, reagent array unit and measurement unit; and, when the current time reaches the exchange date of the major constituent part, the part exchange judging section causes the display unit to display an alarm notifying the exchange of the major constituent part thereon.

In the automatic analyzer, further, it is desirable that the device constant update judging section, when the device constant stored in the memory section is updated, disappears the alarm notifying the update of the device constant on the display unit.

in the automatic analyzer, it is further preferable that the part exchange judging section stores an exchange date of the major constituent part in the test sample array unit, reagent array unit and measurement unit; and, when the current time becomes close to the exchange date of the major constituent part, the part exchange judging section causes the display unit to display a first alarm notifying the exchange of the major constituent part thereon; and, when the current time reaches the exchange date, the part exchange judging section causes the display unit to display of a second alarm notifying the exchange of the major constituent part thereon.

In accordance with another aspect of the present invention, the present invention is constituted so as to attain the above second object in a manner that, an automatic analyzer includes a test sample array unit on which test samples to be tested are arranged, a reagent array unit on which a reagent is arranged, a measurement unit for adding the reagents into the test samples and measuring physical characteristics of the test samples, an input unit for entering a command set by an operator, and a display unit for displaying measured information thereon. The automatic analyzer comprises a standardized protocol control section for controlling the test sample array unit, reagent array unit and measurement unit in accordance with the command entered by the input unit to execute a standardized protocol; a device constant calculation section for calculating a device constant based on the physical characteristic measured by the measurement unit in accordance with the standardized protocol; a memory section for storing the device constant of the automatic analyzer therein; a part exchange judging section for judging whether or not a major constituent part in the test sample array unit, reagent array unit and measurement unit is to be exchanged; a device constant update judging section, when the part exchange judging section judges that the major constituent part is to be exchanged, for judging whether or not a device constant stored in the memory section is to be updated due to the exchange of the major constituent part to cause the display unit to display an alarm notifying update of the device constant; and an analyzing operation control section for controlling operations of the test sample array unit and the reagent array unit in accordance with the command entered by the input unit and for analyzing a specific item for the test sample on the basis of the physical characteristic measured by the measurement unit.

In the automatic analyzer, preferably, the part exchange judging section stores an exchange date of the major constituent part in the test sample array unit, reagent array unit and measurement unit; and, when the current time reaches the exchange date of the major constituent part, the part exchange judging section causes the display unit to display an alarm notifying the exchange of the major constituent part thereon.

In the automatic analyzer, further, it is preferable that the device constant update judging section, when the device constant stored in the memory section is updated, disappears the alarm notifying the update of the device constant on the display unit.

In the automatic analyzer, it is desirable that the part exchange judging section stores an exchange date of the major constituent part in the test sample array unit, reagent array unit and measurement unit; and, when the current time becomes close to the exchange date of the major constituent part, the part exchange judging section causes the display unit to display a first alarm notifying the exchange of the major constituent part thereon; and, when the current time reaches the exchange date, the part exchange judging section causes the display unit to display of a second alarm notifying the exchange of the major constituent part thereon.

In the automatic analyzer, furthermore, it is preferable that the standardized protocol includes at least an enzyme number standardized protocol.

In the automatic analyzer, preferably, the standardized protocol includes an enzyme number standardized protocol, an electrolyte standardized protocol and a cholesterol standardized protocol.

When the part exchange judging section determines that the part should be exchanged, the device constant update judging section judges whether or not to update the device constant due to the part exchange. When the device constant update judging section determines that the device constant should be updated, the command issued from the update judging section causes the display unit to display an alarm notifying the update of the device constant thereon. As a result, a suitable device constant can be stored in the memory section and the physical characteristic of the test sample can be accurately measured.

Further, when the standardized protocol control section causes the standardized protocol to be executed, the device constant calculation section calculates a device constant. Then the calculated device constant is stored in the memory section. The device constant calculation section automatically calculates a device constant with a high accuracy.

DESCRIPTION OF THE PREFERRED EMBODIMENTS

An embodiment of the present invention will now be described with reference to the accompanying drawings.

Figure 1:
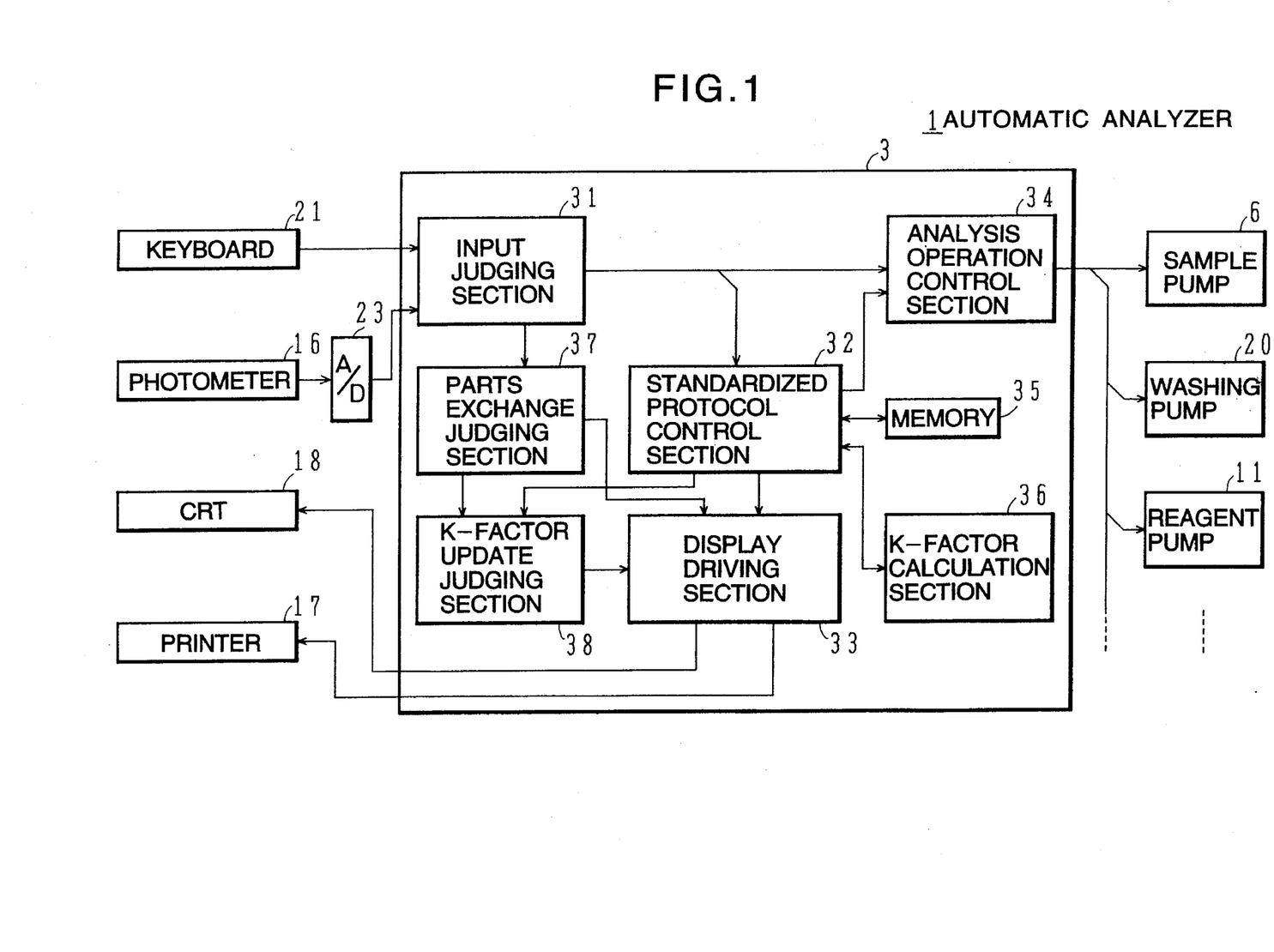
FIG. 1 is a schematic block diagram of a major part of an automatic analyzer in accordance with an embodiment of the present invention.
Figure 2:
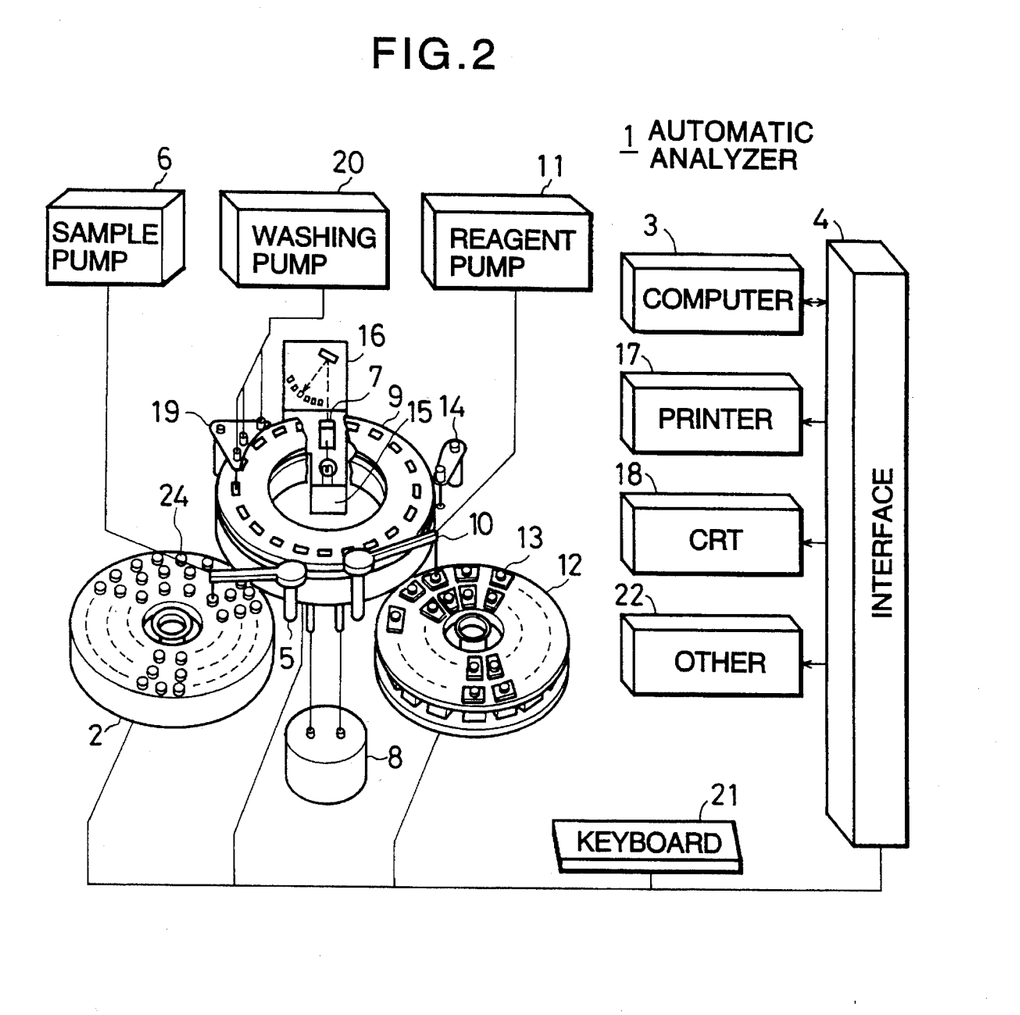
FIG. 2 schematically shows a structure of the entire automatic analyzer of the embodiment of the present invention.

FIG. 1 shows a schematic block diagram of a major part of an automatic analyzer according to the embodiment of the present invention, and FIG. 2 is a schematic perspective view, partly in a block diagram form, an entire arrangement of the automatic analyzer.

Referring first to FIG. 2, a plurality of sample cups 24 containing test sample solutions are arranged on a sample disk (test sample array unit) 2. The operation of the sample disk 2 is controlled by a computer 3 trough an interface 4. When the sample disk 2 is turned to a position where one of the sample cups 24 is disposed below a probe 5 for examination of fractionated test samples (which will hereinafter be referred to merely as the fractionated-test-sample examination probe 5), a sample pump 6 coupled to the fractionated-test-sample examination probe 5 causes the test sample in the one of the sample cups 24 to be fractionated by a predetermined amount into a reaction cuvette 7. The reaction cuvette 7 having the sample fractionated therein is moved to a position for adding a first predetermined reagent (a first reagent addition position) within a reaction bath 9 connected to a thermostat bath 8. A plurality of reagent cuvettes 13 containing the predetermined first reagent are arranged on a reagent disk (reagent array unit) 12. A reagent pump 11 connected to a probe 10 for examining fractionated test reagents (the fractionated-test-reagent examination probe 10) causes the predetermined first reagent to be absorbed or sucked up from one of the reagent cuvettes 13, so that the sucked-up first reagent is discharged into the reaction cuvette 7 having been moved to the first reagent addition position.

The reaction cuvette 7, after the addition of the first reagent thereto, is moved to a position corresponding to a stirring mechanism 14, by which contents of the reaction cuvette 7 is firstly stirred. The reaction cuvette 7 whose contents is thus stirred is irradiated with light emitted from a light source 15. The irradiated light is passed through the reaction cuvette Y, and optical-physical parameters of the contents at this time are detected by a multi-wave length photometer 16. A detection signal of the multi-wave length photometer 16 indicative of the detected optical-physical parameters is supplied to the computer 3 through an analog-to-digital (A/D) converter 23 (omitted in FIG. 2) and the interface 4 and a concentration of an objective substance in the sample is obtained by calculation.

Data indicative of the sample concentration thus obtained by the computer 3 is printed out from a printer (display means) 17 or displayed on a screen of a CRT 18 (display means). The reaction cuvette 7 after the detection is moved to a position corresponding to a washing device 19, by which the solution in the cuvette 7 is discharged by a cuvette washing pump 20, and then washed with a washing solution to get ready for use for the next analysis. Reference numeral 21 denotes a keyboard (input means). When an operator operates the keyboard 21, such a command as an operation start command is executed. Reference numeral 22 denotes other means such as a floppy disk driver.

Referring to FIG. 1, there is shown a functional block diagram of the computer 3 which includes an input judging section 31, a standardized protocol control section 32, a display driving section 33, an analysis operation control section 34, a memory 35, a device constant calculation section 36, a part exchange judging section 37 and a K factor update judging section 38. More specifically, the input judging section 31 judges signals received from the keyboard 21 and the multi-wave length photometer 16, and supplies signals corresponding to the received signals to the standardized protocol control section 32, analysis operation control section 34 or part exchange judging section 37. The standardized protocol control section 32 operates the display driving section 33 in accordance with the signal received from the input judging section 31 to thereby cause the CRT 18 or printer 17 to display or print a predetermined message or the like. Further, the standardized protocol control section 82 supplies a command signal to the analysis operation control section 34 to control the operations of the sample pump 6, washing pump 20, reagent pump 11 and so on. The standardized protocol control section 32 also executes the reading operation of data stored in the memory 35 therefrom or the writing operation of data into the memory. The standardized protocol control section 82 further controls of the operation of the device constant calculation section 36 to store a calculated device constant in the memory 35.

The part exchange judging section 37 judges timings to exchange major constituent parts of the automatic analyzer and, when one of the determined exchange times has come, supplies a command signal to the display driving section 33 to display an alarm notifying a part (e.g., the name of the corresponding part) to be exchanged on the CRT 18. The K factor update judging section 38 is in advance supplied, from the keyboard 21 through the input judging section 31 and part exchange judging section 37, with the numbers of the parts (part numbers) each of which changes the K factor according to the exchange thereof. The K factor update judging section 38 stores therein the part numbers received from the part exchange judging section 37. When one of the parts corresponding to the stored part numbers was exchanged, the K factor update judging section 38 supplies a command signal to the display driving section 33 to display on the CRT 18 an alarming message indicating that the K factor should be updated. After the display of the K-factor update alarming message, the K factor update judging section 38, when receiving a signal representing the completion of re-measurement of a K factor from the standardized protocol control section 32, stops the display of the K-factor update alarming message.

Figure 3:
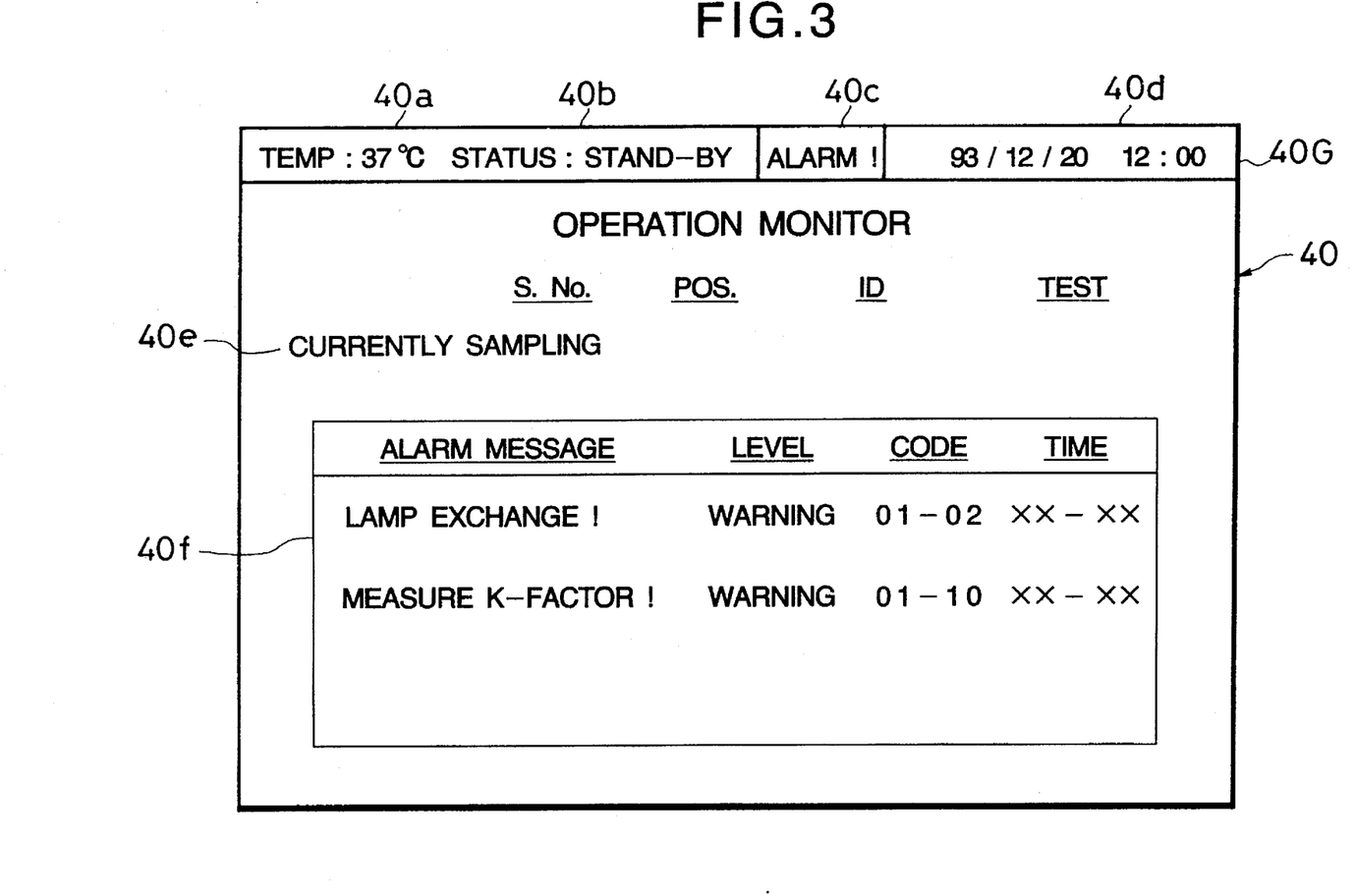
FIG. 3 shows an example of an operation monitor screen in the embodiment of the present invention.

FIG. 3 shows an example of an operation monitor screen (operation-status monitoring screen) 40 of the CRT 18. When the display of another display screen is terminated, this screen 40 is automatically displayed on the CRT 18. In the example of FIG. 3, on a statue line 40G, there are arranged a reaction-bath-temperature monitor part 40a for indicating temperatures of the reaction bath 9, a device status monitor part 40b, an alarm display part 40c and a current date/time display part 40d. When part exchange is necessary, the display color of the alarm display part 40c is changed (e.g., from green to red) or flashed to provide an alarming display for the operator. Indicated in the test sample display part 40e are the sample number (S. No.), array position (Pos.), identifier (ID) and analysis item (Test) of a test sample to be analyzed. Indicated in an alarm message box 40f is contents to be alarmed. In the example of FIG. 3, more specifically, the alarm message box 40f indicates an alarming state notifying the exchange of a lamp and the measurement of the K factor. Also indicated in the alarm message box 40f are codes (01-02 and 01-10 in FIG. 3) which refer to numbers indicative of instruction or explanation manuals stating how to conduct the lamp exchange and how to measure the K factor or the like based on the operation monitor screen 40, the operator can confirm the necessity or non-necessity of the part exchange and the update of the K factor.

Figure 4:
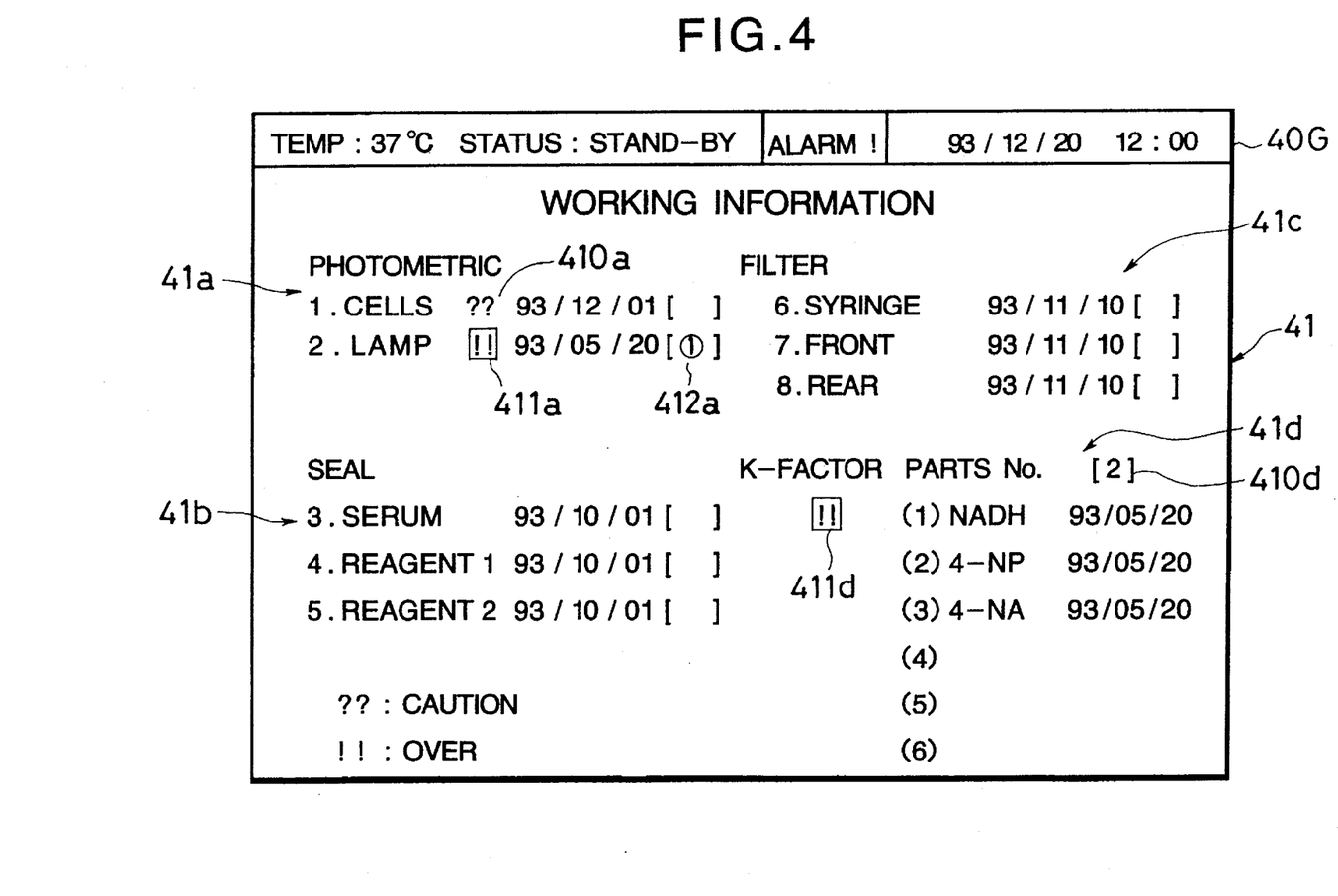
FIG. 4 shows an example of a part exchange/K-factor update management screen in the embodiment of the present invention.

FIG. 4 shows an example of a part exchange/K factor update management screen 41. As in the example of FIG. 3, a status line 40G is displayed in the screen 41. A photometric part indicator part 41a indicates numbers of photometric parts (part numbers) and part names (e.g., cell and lamp) together with their exchange dates. When the current time becomes close to one of the exchange dates, an attention indicating mark "??" (first alarm, that is, an alarm notifying the exchange of the part) appears on the screen 41 between the associated 'part name' and 'exchange date' ( see a display part 410a in FIG. 4). When the current time reaches the exchange date, an exchange alarm indicating mark "!!" (second alarm, that is, an alarm notifying the exchange of the part) appears between the associated 'part name' and 'exchange date' of the part to be exchanged (see an display part 411a in FIG. 4). When the exchange of the associated part is completed, an end indication number representing the completion of the part exchange appears in the vicinity of the exchange date being displayed (in this case, for example, "1" is displayed as shown by a display part 412a in FIG. 4). This is because the part exchange judging section 37 detects the completion of the part exchange through a pushing operation of a key "1" on the keyboard 21.

A seal part display part 41b indicates the names and their numbers of objects for which seal parts are used, together with their exchange dates. Also in the seal part display part 41b, like the display part 41a, the attention indicating mark "??" (first alarm) and exchange alarm indicating mark "!!" (second alarm) are displayed. An end indication number indicative of the completion of the exchange is also displayed.

A filter display part 41c indicates the names and their numbers of objects for which filters are used, together with their exchange dates. Like the display part 41a, also in the filter display part 41c, the attention indicating mark "??" and exchange alarm indicating mark "!!" are displayed. An end indication number indicative of the completion of the exchange is also displayed.

A K factor display part 41d includes a part number set and display part 410d for indicating the part number whose part affects the K factor when exchanged. The display part 410d illustrated in FIG. 4 indicates only a number "2" but a plurality of numbers may be set and displayed if necessary. The display part 41d also indicates the names of reaction inducing substances (standard substances for evaluating a K factor) and their measured dates. When it becomes necessary to update the K factor due to the exchange of the associated part, an update alarm indicating mark (that is, an alarm notifying the update of the K factor) "!!" 411d is displayed. When the K factor is measured and again set, the update alarm indicating mark "!!" disappears.

Figure 5:
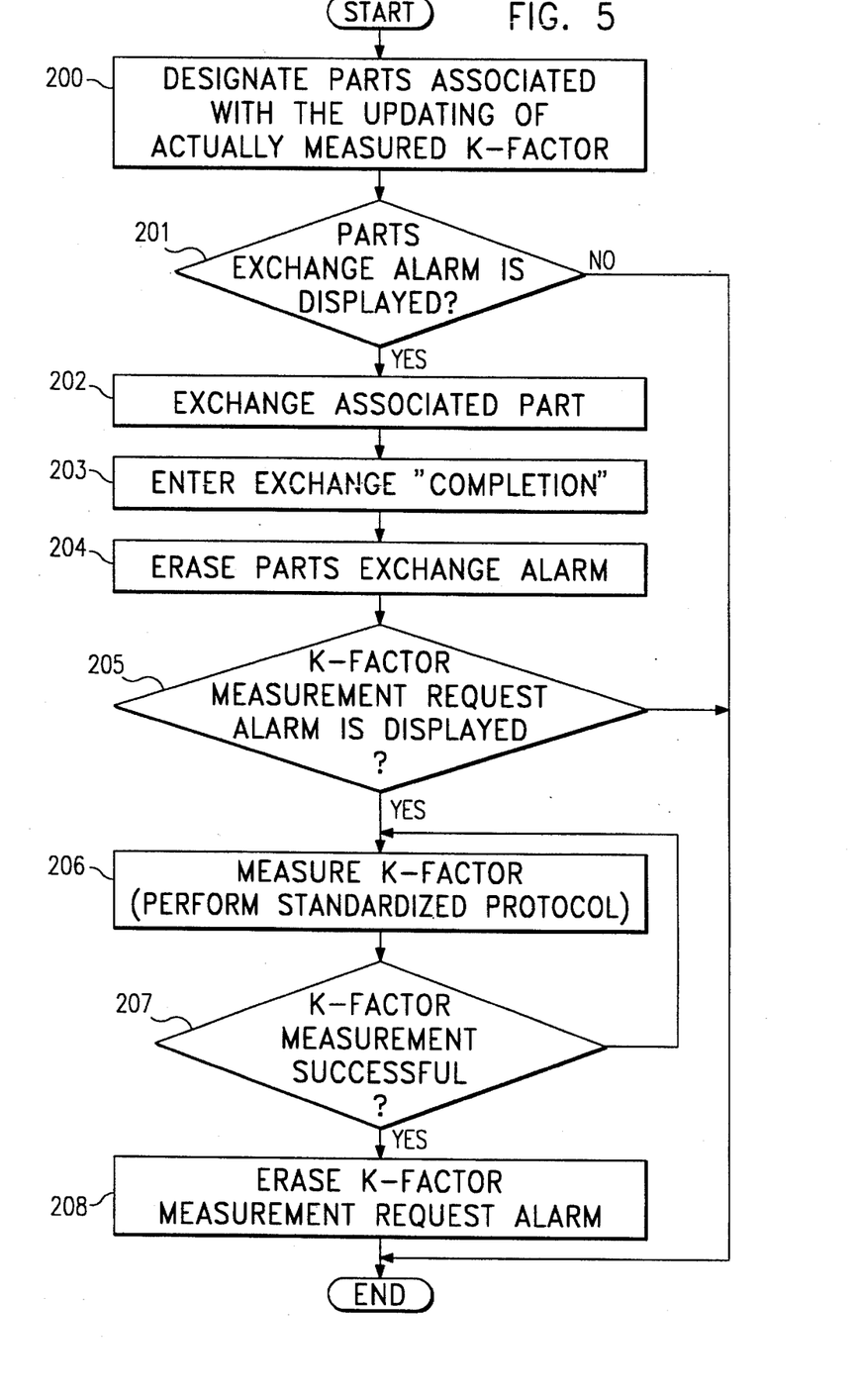
FIG. 5 is a flowchart for explaining the entire operation of the part exchange and K factor update in the embodiment of the present invention.

FIG. 5 is a flowchart for explaining the entire operation of the part exchange and K factor update.

Referring to FIG. 5, in step 200, an operator, after part exchange, designates parts each of which affects the K factor upon exchange thereof through the keyboard 21. Then, in step 201, the operator, based on the display screen 40, checks or judges whether or not the alarm notifying the exchange of the part (part exchange alarm indication) is displayed. In the absence of the part exchange alarm indicating mark on the screen, the processing is terminated. If the part exchange alarm indicating mark is displayed as represented by a YES in step 201, then the processing proceeds to step 202, whereat the operator exchanges the part indicated by the part exchange alarm indicating mark. Subsequently, when completing the part exchange, the operator operates the keyboard 21 in a step 203 to inform the automatic analyzer of the completion of the part exchange. That is, the operator inputs, e.g. a number "1" through the keyboard as mentioned above, then the part exchange alarm indicating mark is automatically disappeared in step 204.

In step 205, the operator checks the presence or absence of an alarm notifying the measurement of the K factor, i.e., the update alarm indicating mark "!!" on the screen. In the absence of such an update alarm indicating mark, the processing is terminated. If the update alarm indicating mark "!!" is displayed on the screen as represented by a YES in step 205, the processing proceeds to step 206, whereat the K factor is measured. Then, it is judged in step 207 whether or not the measurement of the K factor was successful. If the measurement of the K factor was not successful, the processing returns to step 206. In contrast, if the measurement of the K factor was successful, the processing proceeds to step 208, whereat the update alarm indicating mark "!!" with respect to the K factor is erased from the screen and the processing is terminated.

Figure 6:
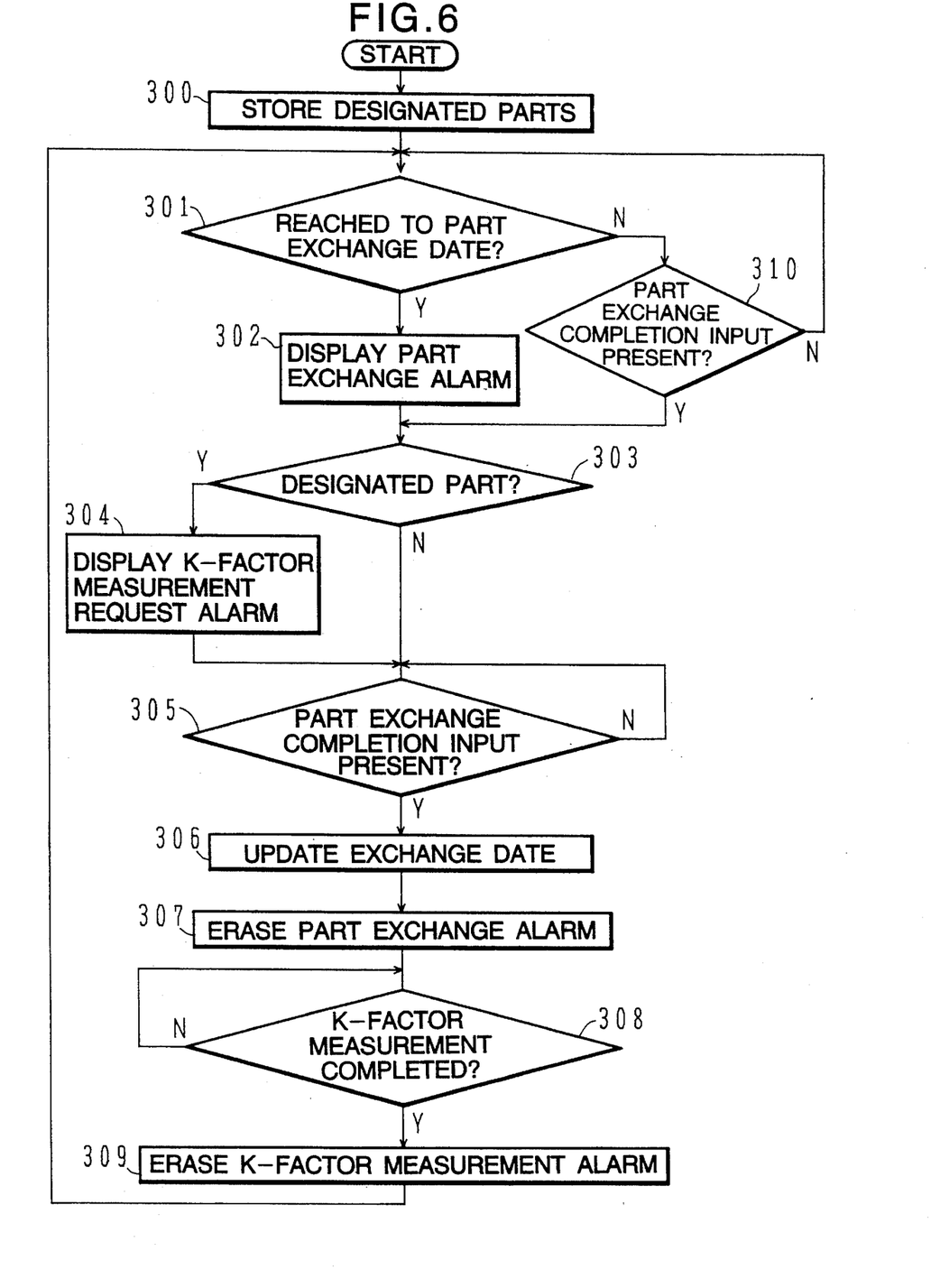
FIG. 6 is a flowchart for explaining the operations of a part exchange judging section and a K-factor update judging section in the embodiment of the present invention.

FIG. 6 is a flowchart for explaining the operations of the part exchange judging section 37 and K factor update judging section 38 in the computer 3.

Referring to FIG. 6, in step 301, the K factor update judging section 38 stores the numbers of the parts (part numbers) each of which affects the K factor due to the exchange thereof and which are designated by the operator through the keyboard 21. Then the part exchange judging section 37 judges in step 301 whether or not the current time has reached one of the exchange dates of the parts stored therein on the basis of a timer (software timer) built in the computer 3. If it is judged that the current time has not reached any of stored exchange dates, the processing of the part exchange judging section 37 proceeds to step 310 to judge the presence or absence of a part exchange completion input. This input is provided because the part may be exchanged for some reason other than the arrival of the part exchange date. If it is judged that the part exchange completion input is absent in step 310, the processing returns to step 301. In contrast, if it is judged that the part exchange completion input is present in step 310, the processing proceeds to step 303.

If it is judged that the current time has reached one of the exchange dates in step 301, the processing proceeds to step 302. In step 302, the part exchange judging section 37 supplies a command signal to the display driving section 33 to display the part exchange alarm indicating mark (first or second alarm indicating mark) on the CRT 18. Then in step 303, the K factor update judging section 38 judges, on the basis of a signal indicative of an exchange part name received from the part exchange judging section 37, whether or not the part to be exchanged corresponds to the part number designated in step 300. If it is judged in step 303 that the part to be exchanged is not the one designated in step 300, the processing proceeds to step 305. If it is judged in step 303 that the part to be exchanged is the one designated in step 300, the processing proceeds to step 304, whereat the K factor update judging section 38 supplies the command signal to the display driving section 33 to display the K-factor measurement request alarm indicating mark on the CRT 18.

In step 305, the part exchange judging section 37 judges whether or not the part exchange completion input is received. If it is judged that the part exchange completion input is received, the processing proceeds to step 306. In step 306, the part exchange judging section 37 updates the exchange date of the part having been exchanged. Then the processing proceeds to step 307, whereat the part exchange judging section 37 supplies a command signal to the display driving section 33 to cause the part exchange alarm indicating mark to disappear on the CRT. Then the processing proceeds to step 308, whereat the K factor update judging section 38 judges, on the basis of a signal received from the standardized protocol control section 32, whether or not the measurement of the K factor is completed. If it is judged that the measurement of the K-factor is completed, the processing proceeds to step 309. In step 309, the K factor update judging section 38 supplies a command signal to the display driving section 33 to cause the K-factor measurement request alarm indicating mark to disappear on the CRT. Then the processing returns to step 301.

Explanation will next be made as to the operation of the standardized protocol.

Figure 7:
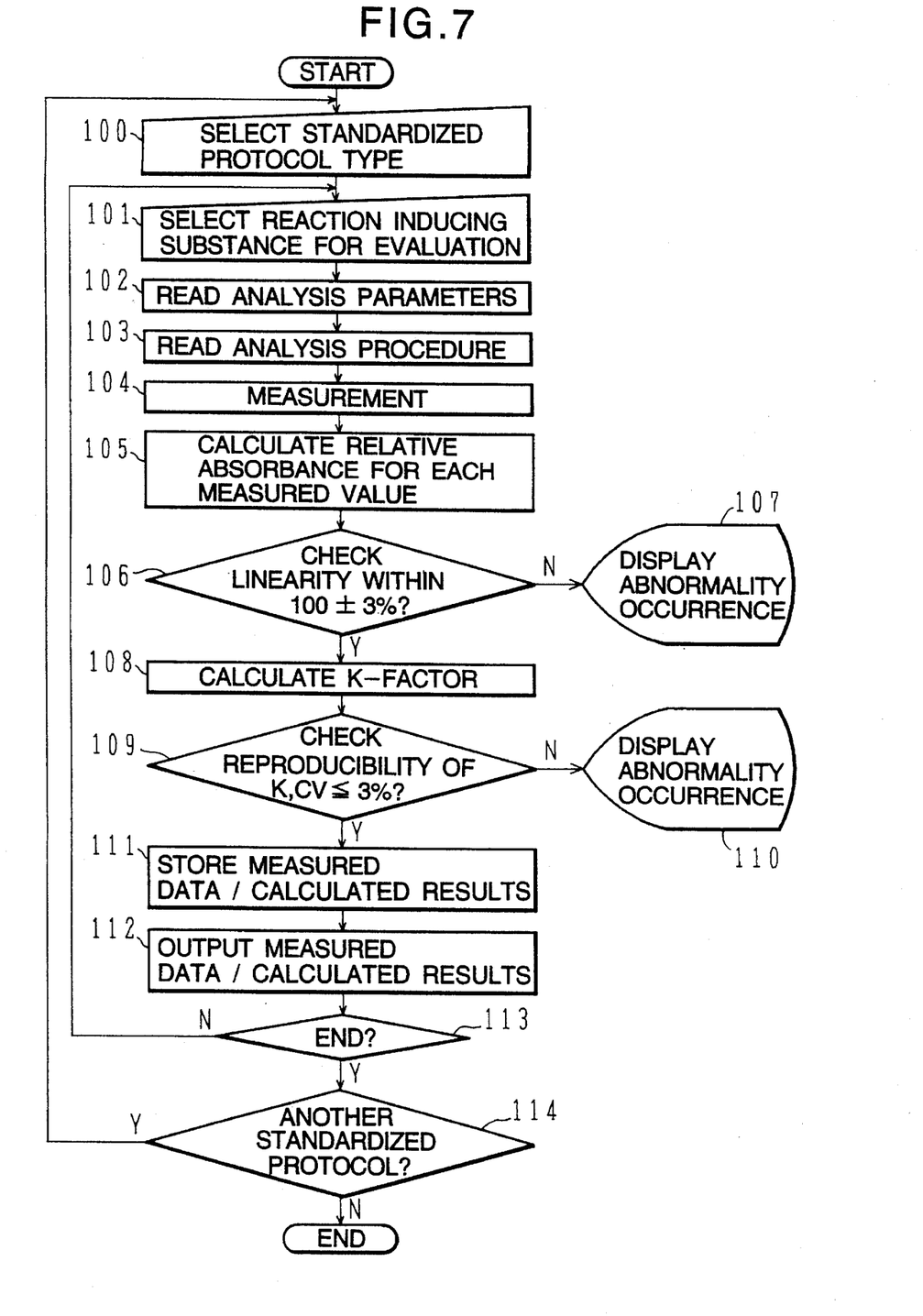
FIG. 7 is a flowchart for explaining the K-factor calculating operation in the embodiment of the present invention.
Figure 8:
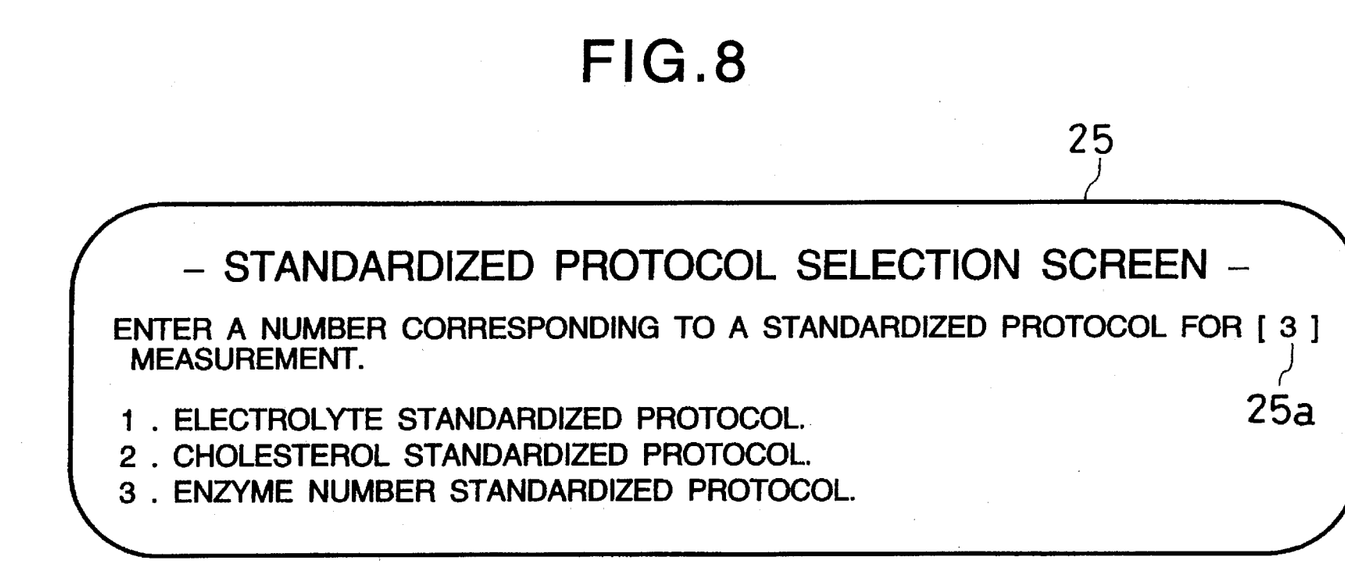
FIG. 8 shows an example of a standardized protocol selection screen in the embodiment of the present invention.
Figure 9:
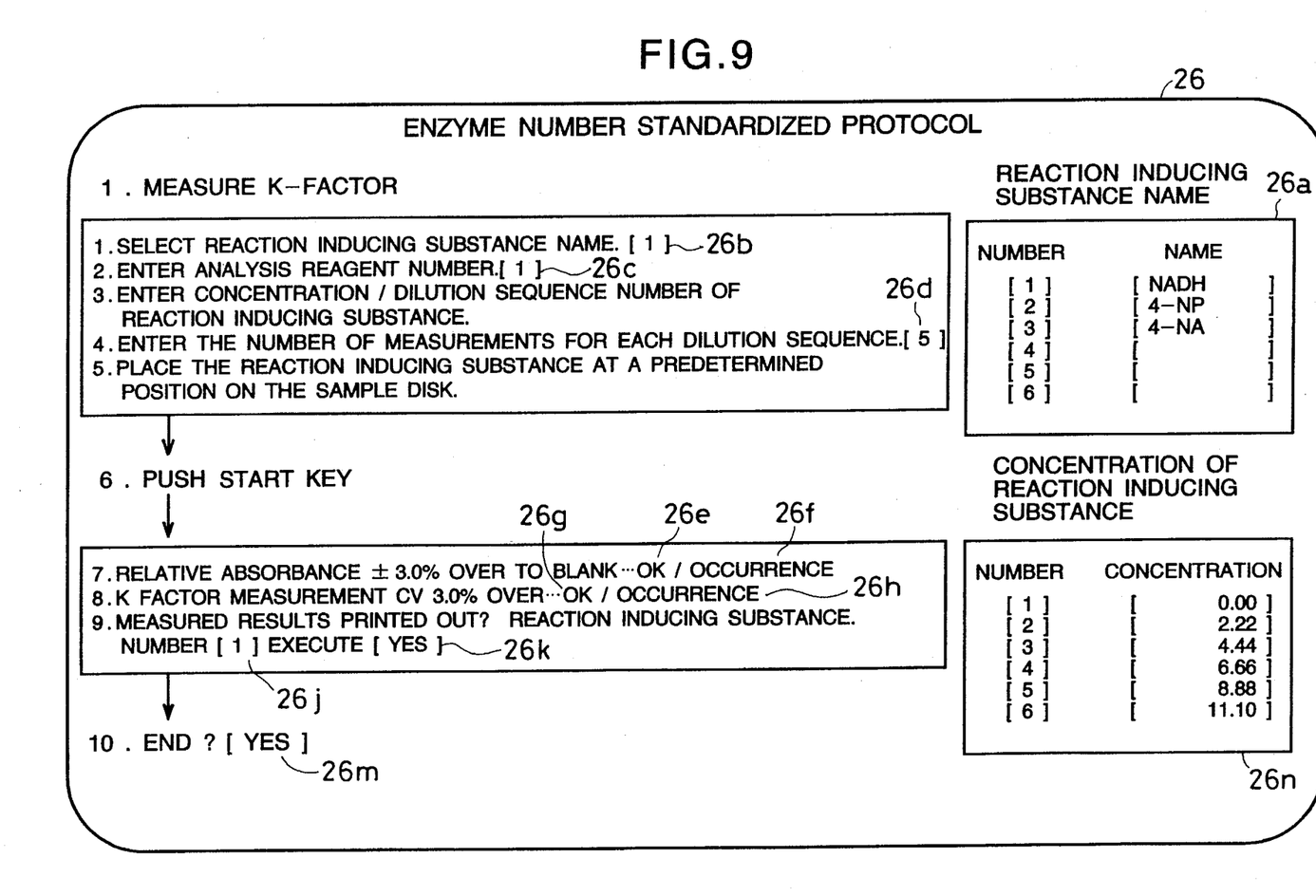
FIG. 9 shows an example of an enzyme number standardized protocol selection screen in the embodiment of the present invention.

The operation of the standardized protocol control is shown as a flowchart in FIG. 7. Referring to FIG. 7, the type of a standardized protocol is selected in step 100. That is, the operator pushes a key indicative of the start of a standardized protocol on the keyboard 21, which is then recognized by the input judging section 31. Then the standardized protocol control section 32 operates the display driving section 33 to display such a standardized protocol selection screen 25 as shown in FIG. 8 on the CRT 18. On the standardized protocol selection screen 25, there are displayed 1. an electrolyte standardized protocol, 2. a cholesterol standardized protocol, and 3. an enzyme number standardized protocol. Then, the operator inputs a number corresponding to desired one of these standardized protocols through the keyboard 21 in accordance with a message "Enter a number corresponding to desired one of the standardized protocols." For example, when the operator selects a number "3" indicative of the enzyme number standardized protocol, a selection number "3" is indicated at a number display part 25a in the screen 25. Subsequently, such an enzyme number standardized protocol screen (measurement procedure screen) 26 as shown in FIG. 9 is displayed on the CRT 18.

In next step 101, one of reaction inducing substances on the screen 26 is selected from the screen 26 through the keyboard 21. In this case, the operator enters through the keyboard a number indicative of desired one of the reaction inducing substances displayed at a reaction inducing substance name display part 26a on the upper right of the screen 26 in accordance with a displayed message "Select one of the reaction inducing substances." For example, when the operator selects NADH as the reaction inducing substance and enters a number "1", a selection number [1] appears at a selected reaction inducing substance display part 26b. Next, the processing proceeds to step 102, whereat analysis parameters are input. First, the operator enters an analysis reagent (analysis item) number in accordance with a displayed message "Enter an analysis reagent number." If the operator selects AST as the analysis reagent, then the operator enters an analysis item number "1", whereby a selection number [1] is displayed at a reagent number display part 26c.

In step 103, an analysis procedure is set or entered. That is, the operator enters a concentration of the reaction inducing substance, a dilution sequence number and the number of measurements for each dilution sequence in accordance with displayed messages "Enter a concentration of the reaction inducing substance concentration and a dilution sequence number" and "Enter the number of measurements for each dilution sequence." For example, when the dilution sequence of the reaction inducing substance has 6 concentrations of 0.0–0 mM, 2.22 mM, 4.44 mM, 6.66 mM, 8.88 mM and 11.10 mM and the number of measurements for each dilution sequence is 5, the above 6 concentrations are displayed at a reaction inducing substance concentration selection display part 26n and a selection measurement number [5] is displayed at a measurement number display part 26d.

Next, the processing proceeds to step 104, whereat the measurement is initiated. That is, the reaction inducing substance is set at a predetermined position on the sample disk 2 in accordance with a message "Place the reaction inducing substance at a predetermined position on the sample disk" displayed on the screen. Then, the operator pushes a START key on the keyboard 21 in accordance with a displayed message "Push the START key.", whereby the standardized protocol control section 32 supplies a command signal to the analysis operation control section 34. Then the analysis operation control section 34 controls the operations of the sample pump 6, washing pump 20, reagent pump 11 and so on to perform the standardized protocol. The position of the reaction inducing substance set on the sample disk 2 is previously stored in the memory 35 of the computer 3 as a constant and may be changed by rewriting the contents of the memory 35.

In next step 105, a relative absorbance for each measured value is calculated. That is, a signal indicative of a quantity of light measured by the multi-wave length photometer 16 is supplied to the standardized protocol control section 32 through the A/D converter 23 and input judging section 31. Then the standardized protocol control section 32 operates the device constant calculation section 36 to calculate a relative absorbance for each sample. The relative absorbance represents a relative value of the absorbance of another measured sample with respect to the absorbance of one of the measured samples having the lowest concentration when the latter absorbance is set at 100%. In step 106, the linearity of the relative absorbance obtained in step 105 is checked. That is, it is judged whether or not the relative absorbance is within 100±3%. If it is judged that the relative absorbance is not within 100±3%, the standardized protocol control section 32 causes the display driving section 33 to display a message indicative of abnormality occurrence on the CRT 18 (an indication "occurrence" appears at an abnormality display part 36f as shown in FIG. 9). In contrast, if it is judged that the relative absorbance is within 100±3%, the standardized protocol control section 32 causes the display driving section 33 to display a message indicative of normality on the CRT 18 (an indication "OK" appears at a normality display part 26c as shown in FIG. 9), and the processing proceeds to step 108.

In step 108, the device constant calculation section 36 calculates a device constant K (K factor). The device constant K, which is obtained by dividing the displayed concentration of the measurement sample by a blank correction absorbance, is calculated for each measurement sample. The device constant calculation section 36 also calculates an average value of such calculated device constants K and a standard deviation SD thereof. In next step 109, the device constants K are checked with respect to reproducibility. That is, it is checked whether or not the dispersion or variation CV of the device constants K is within 3.0%. If it is checked that the dispersion CV is not within 3.0%, then a message indicating the occurrence of abnormality is displayed in step 110 as "occurrence" at an abnormality display part 26h on the CRT 18. If it is checked that the dispersion CV is within 3.0%, then a message indicative of normality is displayed on the CRT 18 as an indication "OK" at the abnormality display part 26h and the processing proceeds to step 111. In step 111, measured data and calculation results are stored in the memory 35.

Figure 10:
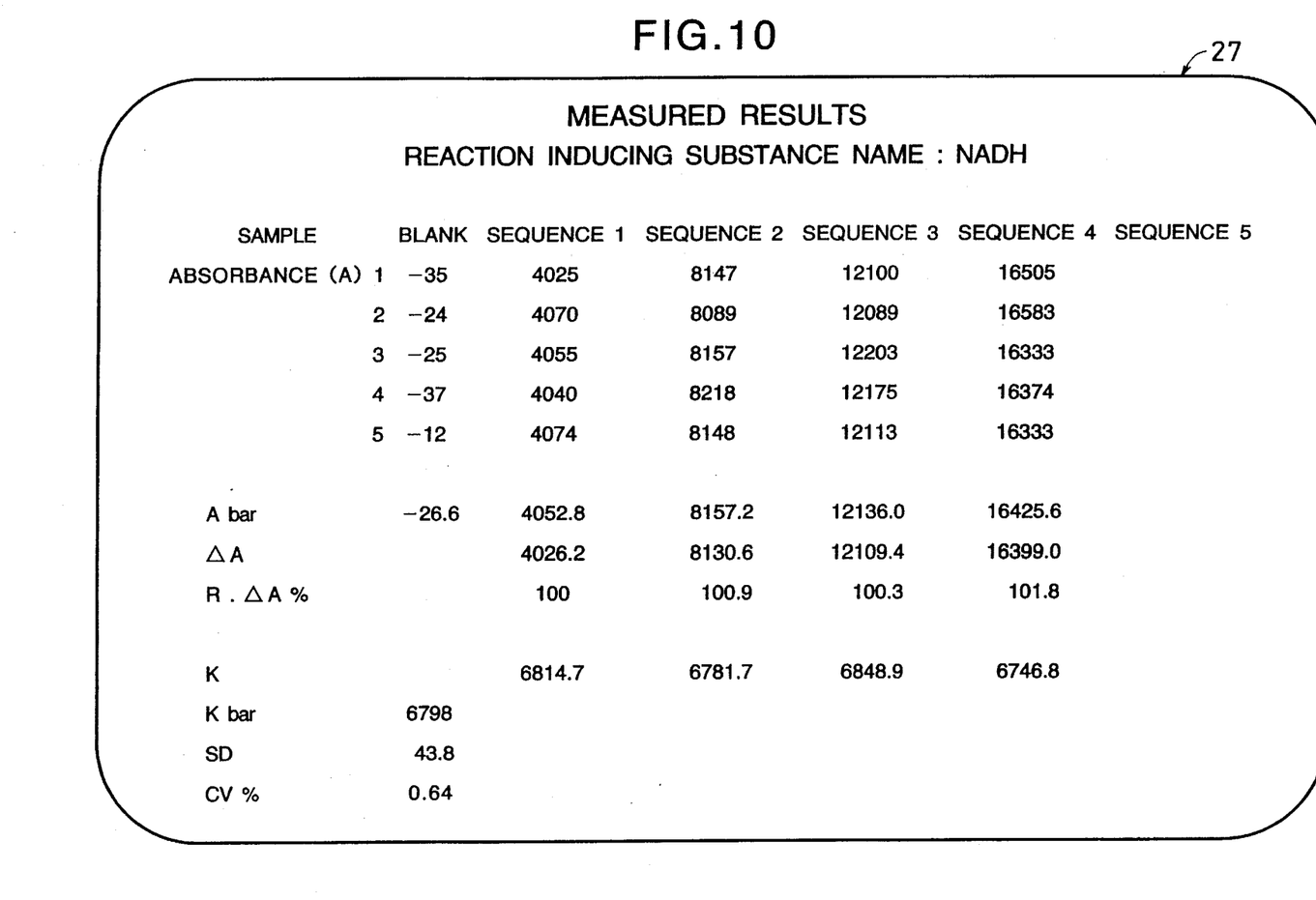
FIG. 10 shows an example of a display or a print-out of measured results based on the standardized protocol in the embodiment of the present invention.

In next step 112, a message "Are the measured results printed out?" is displayed to inquire of the operator about whether or not to output the measured data and calculated results. If the operator wished to output the measured data and calculated results, then the operator inputs the reaction inducing substance number and "YES" indicative of the output through the keyboard 21, which results in that a number [1] is displayed at a number display part 26j and a symbol [YES] is displayed at an execution display part 26k. As a consequence, the standardized protocol control section 32 reads out the data corresponding to the input reaction inducing substance number from the memory 35. Then the standardized protocol control section 32 causes the display driving section 33 to be driven so that the measured data and calculated results, e.g., a calculation result screen 27 as shown in FIG. 10 are output onto the CRT 18 or from the printer 17. In FIG. 10, Abar denotes an average value of absorbances, ΔA denotes a value obtained by subtracting a blank value of Abar from the Abar, R.ΔA% denotes a relative absorbance, K denotes a device constant, Kbar denotes an average value of the device constants K, SD denotes a standard deviation of the device constants K, CV% denotes dispersion (SD·100/Kbar).

The processing proceeds to step 113, whereat it is judged whether or not to measure another reaction inducing substance. If it is judged to measure another reaction inducing substance, a symbol [NO] is displayed at an display part 26m, and the processing returns to step 101. If it is judged not to measure another reaction inducing substance in the step 113, a symbol [YES] is displayed at the display part 26m, and the processing proceeds to step 114 to judge whether or not to perform another standardized protocol. If it is judged not to perform another standardized protocol, the operation is ended. In contrast, if it is judged to perform another standardized protocol, the processing returns to step 100.

In this way, analysis of enzyme or the like in a sample to be tested is carried out by using the calculated device constant.

Therefore, according to the foregoing embodiment of the present invention, the part exchange judging section 37 judges the necessity or non-necessity of part exchange and when it is judged that part exchange is necessary, the part exchange alarm indicating mark is displayed on the display screen. Then the K factor update judging section 38 judges whether or not the part to be exchanged is the one that affects the K factor. If so, the K-factor update alarm indicating mark is displayed. This K-factor update alarm indicating mark is displayed until the K factor is updated. As a result, the test sample can be measured by using a suitable K factor, and thus measuring accuracy of characteristics of the test sample can be improved.

Further, according to the embodiment of the present invention, various kinds of standardized protocols can be automatically carried out. Accordingly, management of part exchange can be facilitated and calculation accuracy of the K factor can be improved.

While the K factor has been automatically measured and calculated in the foregoing embodiment, the present invention may be configured such that an external calculator is employed to calculate the K factor manually and the K factor is entered from the keyboard and input into an internal memory of the automatic analyzer.

Further, although, in the above-described embodiment, three of the electrolyte standardized protocol, cholesterol standardized protocol and enzyme number standardized protocol have been used as standardized protocols in the foregoing embodiment, the present invention is not limited to the specific example. For example, another standardized protocol such as a glucose standardized protocol may be employed.

Furthermore, although, in the foregoing embodiment, such a screen 26 has been arranged as a screen for instructing the operation of the standardized protocol, the present invention is not restricted to the specific example and another arrangement may be employed. For example, a flowchart indicative of the operation of the standardized protocol together with a selected substance number or the like may be displayed on the screen.

What is claimed is:

1. An automatic clinical analyzer including a test sample array unit on which test samples to be tested are arranged, a reagent array unit on which reagents are arranged, a measurement unit for adding said reagents into said test samples and measuring physical characteristics of the test samples, input means for entering a command set by an operator, and display means for displaying measured information thereon, said automatic clinical analyzer comprising:

a memory section for storing a device constant of said automatic clinical analyzer therein;

a part exchange judging section for judging whether or not a major constituent part in said test sample array unit, reagent array unit and measurement unit is to be exchanged;

a device constant update judging section, when said part exchange judging section judges that the major constituent part is to be exchanged, for judging whether or not a device constant stored in said memory section is to be updated due to the exchange of the major constituent part to cause said display means to display an alarm notifying update of the device constant; and an analyzing operation control section for controlling operations of said test sample array unit and said reagent array unit in accordance with the command entered by said input means and for analyzing a specific item for the test sample on the basis of the physical characteristic measured by said measurement unit.

2. An automatic clinical analyzer according to claim 1, wherein said part exchange judging section stores an exchange date of the major constituent part in said test sample array unit, reagent array unit and measurement unit; and, when the current time reaches said exchange date of the major constituent part, said part exchange judging section causes said display means to display an alarm notifying the exchange of the major constituent part thereon.

3. An automatic clinical analyzer according to claim 1, wherein said device constant update judging section, when the device constant stored in said memory section is updated, clears the alarm notifying the update of the device constant on said display means.

4. An automatic clinical analyzer according to claim 1, wherein said part exchange judging section stores an exchange date of the major constituent part in said test sample array means, reagent array unit and measurement unit; and, when the current time becomes close to said exchange date of the major constituent part, said part exchange judging section causes said display means to display a first alarm notifying the exchange of the major constituent part thereon; and, when the current time reaches said exchange date, said part exchange judging section causes the display means to display of a second alarm notifying the exchange of the major constituent part thereon.

5. An automatic clinical analyzer including a test sample array unit on which test samples to be tested are arranged, a reagent array unit on which reagents are arranged, a measurement unit for adding said reagents into said test samples and measuring physical characteristics of the test samples, input means for entering a command set by an operator, and display means for displaying measured information thereon, said automatic clinical analyzer comprising:

a standardized protocol control section for controlling said test sample array unit, reagent array unit and measurement unit in accordance with the command entered by said input means to execute a standardized protocol;

a device constant calculation section for calculating a device constant based on the physical characteristic measured by said measurement unit in accordance with said standardized protocol;

a memory section for storing said device constant of said automatic clinical analyzer therein;

a part exchange judging section for judging whether or not a major constituent part in said test sample array unit, reagent array unit and measurement unit is to be exchanged;

a device constant update judging section, when said part exchange judging section judges that the major constituent part is to be exchanged, for judging whether or not a device constant stored in said memory section is to be updated due to the exchange of the major constituent part to cause said display means to display an alarm notifying update of the device constant; and an analyzing operation control section for controlling operations of said test sample array unit and said reagent array unit in accordance with the command entered by said input means and for analyzing a specific item for the test sample on the basis of the physical characteristic measured by said measurement unit.

6. An automatic clinical analyzer according to claim 5, wherein said part exchange judging section stores an exchange date of the major constituent part in said test sample array unit, reagent array unit and measurement unit; and, when the current time reaches said exchange date of the major constituent part, said part exchange judging section causes said display means to display an alarm notifying the exchange of the major constituent part thereon.

7. An automatic clinical analyzer according to claim 5, wherein said device constant update judging section, when the device constant stored in said memory section is updated, clears the alarm notifying the update of the device constant on said display means.

8. An automatic clinical analyzer according to claim 5, wherein said part exchange judging section stores an exchange date of the major constituent part in said test sample array means, reagent array unit and measurement unit; and, when the current time becomes close to said exchange date of the major constituent part, said part exchange judging section causes said display means to display a first alarm notifying the exchange of the major constituent part thereon; and, when the current time reaches said exchange date, said part exchange judging section causes the display means to display of a second alarm notifying the exchange of the major constituent part thereon.

9. An automatic clinical analyzer according to claim 5, wherein said standardized protocol includes at least an enzyme number standardized protocol.

10. An automatic clinical analyzer according to claim 5, wherein said standardized protocol includes an enzyme number standardized protocol, an electrolyte standardized protocol and a cholesterol standardized protocol.

* * * * *